(12) United States Patent
Auckenthaler et al.

(10) Patent No.: US 9,772,273 B2
(45) Date of Patent: Sep. 26, 2017

(54) METHOD AND DEVICE FOR MONITORING A HUMIDITY SENSOR IN A COMBUSTION ENGINE, USING OXYGEN MEASUREMENT OF OTHER SENSORS IN THE ENGINE, SUCH AS NOX, LAMBDA AND/OR OXYGEN SENSORS

(75) Inventors: Theophil Auckenthaler, St. Gallen (CH); Werner Zaehner, Rehetobel (CH)

(73) Assignee: FPT MOTORENFORSCHUNG AG, Arbon (CH)

( * ) Notice: Subject to any disclaimer, the term of this patent is extended or adjusted under 35 U.S.C. 154(b) by 409 days.

(21) Appl. No.: 13/261,495

(22) PCT Filed: May 5, 2011

(86) PCT No.: PCT/EP2011/057189
§ 371 (c)(1),
(2), (4) Date: Feb. 1, 2013

(87) PCT Pub. No.: WO2011/138387
PCT Pub. Date: Nov. 10, 2011

(65) Prior Publication Data
US 2013/0118232 A1    May 16, 2013

(30) Foreign Application Priority Data
May 6, 2010 (EP) .................................. 10162087

(51) Int. Cl.
*G01N 19/10* (2006.01)
*F02D 41/22* (2006.01)
*F02D 41/14* (2006.01)

(52) U.S. Cl.
CPC ........... *G01N 19/10* (2013.01); *F02D 41/222* (2013.01); *F02D 41/146* (2013.01);
(Continued)

(58) Field of Classification Search
CPC ... G01N 19/10; F04D 41/222; F04D 41/1454; F04D 41/146; F04D 2200/0418; Y02T 10/40
(Continued)

(56) References Cited

U.S. PATENT DOCUMENTS 5,735,245 A   4/1998 Kubesh et al.
6,575,148 B1  6/2003 Bhargava et al.
(Continued)

FOREIGN PATENT DOCUMENTS

CN   1241470   1/2000
CN   2375963   4/2000
(Continued)

*Primary Examiner* — Daniel S Larkin
*Assistant Examiner* — Irving A Campbell
(74) *Attorney, Agent, or Firm* — Stetina Brunda Garred and Brucker

(57) ABSTRACT

The present invention provides for a method and device for monitoring an ambient humidity sensor in a combustion engine, where the monitoring of the ambient humidity sensor is made by comparing the ambient humidity measured by said humidity sensor and an ambient humidity determined from an oxygen measurement of at least another sensor in the engine system, such as a NOX, or Lambda and/or an oxygen sensor. Said comparison is made using an offset of the oxygen signal reading of said at least another sensor, in a fuel cut condition where the drift or offset of said another sensor is related to the variation of the ambient humidity.

4 Claims, 2 Drawing Sheets

(52) U.S. Cl.
CPC .. *F02D 41/1454* (2013.01); *F02D 2200/0418* (2013.01); *Y02T 10/40* (2013.01)

(58) Field of Classification Search
USPC ........... 73/1.06, 23.31, 29.01, 29.02, 114.31, 73/114.69, 114.73; 60/605.2; 123/344, 123/349, 434, 563, 568.11, 568.16, 123/568.21, 568.22, 690; 700/276; 701/1, 2, 25, 33.1, 33.4, 36, 41, 45, 48, 701/49, 70, 102, 103, 104, 117, 301, 400, 701/425, 427, 431, 537, 540
See application file for complete search history.

(56) References Cited

U.S. PATENT DOCUMENTS

| | | | |
|---|---|---|---|
| 6,899,090 | B2 | 5/2005 | Arnold |
| 7,063,668 | B2 * | 6/2006 | Cardelius ............... A61M 16/12 128/204.22 |
| 2004/0050375 | A1 | 3/2004 | Arnold |
| 2005/0072411 | A1 | 4/2005 | Cullen |
| 2009/0254245 | A1 | 10/2009 | Bauerle |
| 2010/0064685 | A1 * | 3/2010 | Auffret ............... F02B 29/0412 60/602 |
| 2010/0139245 | A1 | 6/2010 | Scheuerer |
| 2011/0131957 | A1 * | 6/2011 | Hepburn ................. F01N 3/021 60/278 |
| 2011/0132340 | A1 * | 6/2011 | Soltis ............................ 123/703 |

FOREIGN PATENT DOCUMENTS

| | | |
|---|---|---|
| DE | 102007053719 | 6/2009 |
| EP | 1203878 | 5/2002 |
| EP | 1286035 A2 | 2/2003 |
| EP | 1288455 | 3/2003 |
| JP | S622149 | 1/1987 |
| JP | S62203942 | 9/1987 |
| JP | S6412258 | 1/1989 |
| JP | H06272593 | 9/1994 |
| JP | 2003172192 | 6/2003 |
| JP | 2003328823 | 11/2003 |
| JP | 20050330358 | 2/2005 |
| JP | 2005188369 | 7/2005 |
| JP | 2009007934 | 1/2009 |
| JP | 2009264341 | 11/2009 |

\* cited by examiner

METHOD AND DEVICE FOR MONITORING A HUMIDITY SENSOR IN A COMBUSTION ENGINE, USING OXYGEN MEASUREMENT OF OTHER SENSORS IN THE ENGINE, SUCH AS NOX, LAMBDA AND/OR OXYGEN SENSORS

FIELD OF THE INVENTION

The present invention relates to a method and device for monitoring a humidity sensor in a combustion engine, using oxygen measurement of other sensors in the engine, such as NOx, lambda and/or oxygen sensor.

DESCRIPTION OF THE PRIOR ART

The NOx emissions of an internal combustion engine are significantly influenced by the humidity of the ambient air. For example in central Europe, variations of the ambient humidity between summer and winter may lead to variations of the NOx emissions of up to 20%.

Therefore, a sensor can be used in order to correct for the influence of the ambient humidity in concepts, where the raw NOx emissions are calculated instead of using an NOx sensor. The relative or absolute humidity of the ambient air is measured with a humidity sensor, in order to be able to accurately predict the NOx emissions of the engine. This renders the humidity sensor an emission relevant component, hence it has to be monitored and checked against an independent calculation/sensor, as the emission regulations and legislation impose the monitoring of all components which have an influence on the emissions.

Generally a sensor monitoring is established using redundant information from two or more independent sources such as measurements and/or models, the reading of which can be checked against each other. However the monitoring of an ambient humidity sensor is particularly difficult, because no obvious device can be used for a redundant determination of the ambient humidity.

In the case of NOx emissions, the comparison of the calculated NOx emissions against measured ones is mandatory, if only one NOx sensor is used in the exhaust gas line. This comparison is necessary to monitor the reliability of the NOx sensor reading. However the humidity sensor cannot be monitored simultaneously and independently this way. In addition the use of more than one humidity sensor is obviously costly and therefore should be avoided.

A possible solution for checking the ambient humidity should be the use of more than one NOx sensor. However, in this case, the use of an ambient humidity sensor is not necessary anymore.

SUMMARY OF THE INVENTION

Therefore it is the main object of the present invention to provide a method and device for monitoring a humidity sensor in a combustion engine, which overcomes the above problems/drawbacks.

The basic idea of the invention is the monitoring of an ambient humidity sensor in a combustion engine by determination of the ambient humidity from the oxygen measurement of other sensors in the engine, such as NOx, lambda and/or oxygen sensor.

These and further objects are achieved by means of a method and device for monitoring a humidity sensor in a combustion engine, using oxygen measurement of other sensors in the engine, such as NOx, lambda and/or oxygen sensors, as described in the attached claims, which form an integral part of the present description.

BRIEF DESCRIPTION OF THE DRAWINGS

The invention will become fully clear from the following detailed description, given by way of a mere exemplifying and non limiting example, to be read with reference to the attached drawing figures, wherein.

DETAILED DESCRIPTION OF THE PREFERRED EMBODIMENTS

Figure 1:
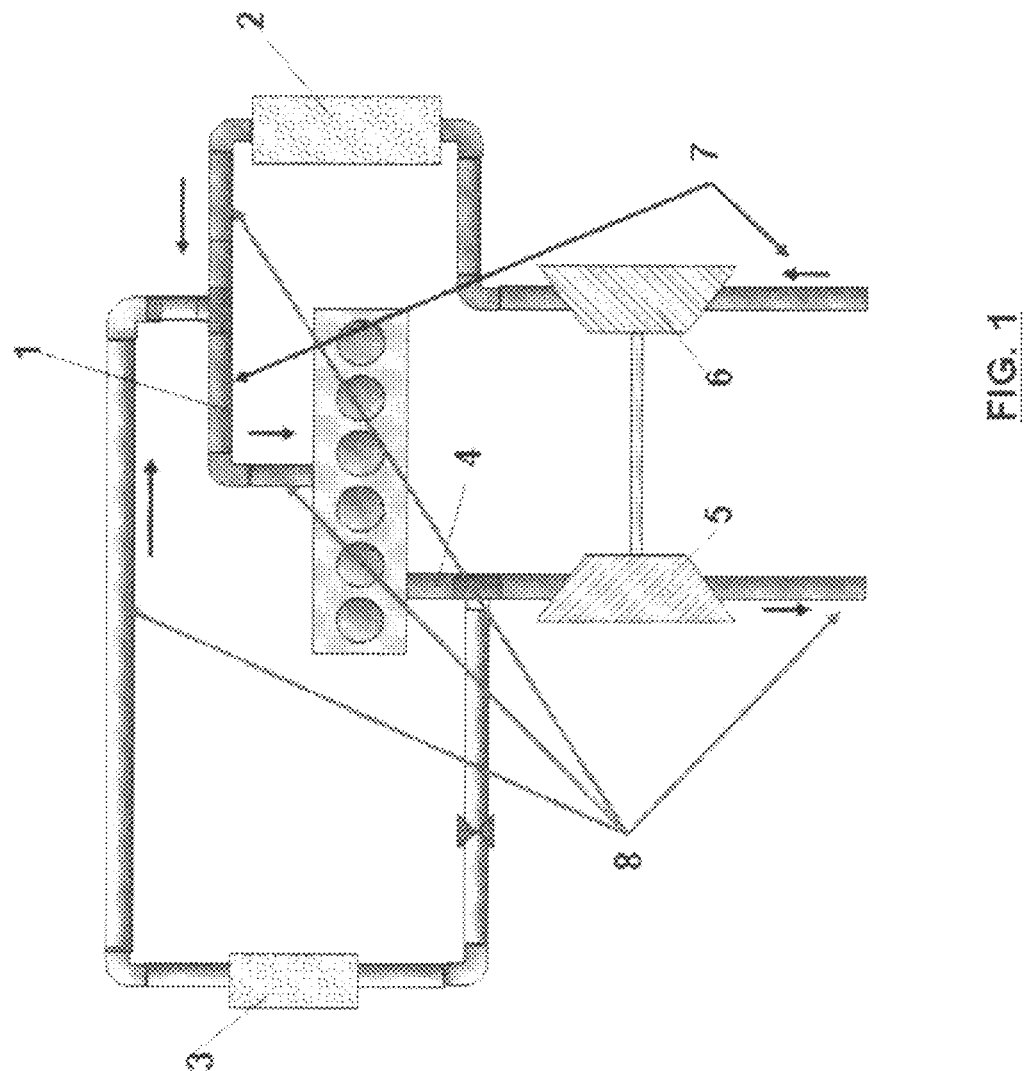
FIG. 1 shows a scheme of an engine system where the invention applies.

The main influence of the ambient humidity on the NOx emissions actually reflects the decreasing availability of oxygen in case of increasing humidity. In other words, the oxygen concentration in the ambient air decreases with increasing humidity. Therefore, the local flame temperature decreases in the cylinder, which eventually leads to lower NOx emissions.

In many engine management systems, NOx, lambda or oxygen sensors are used in the exhaust of the engines. During fuel cut-off phases, i.e., when the fuel injection is shut off, for example when the vehicle is driving downhill, lambda and/or oxygen sensors measure the oxygen concentration of the ambient air. This oxygen concentration is obviously dependent on the ambient humidity.

Therefore, in summary, the NOx, lambda or oxygen sensor provides an independent information about the level of the ambient humidity, which can be used to monitor the reliability of the ambient humidity signal.

More particularly, in many engine management systems, the use of an NOx sensor is mandatory in order to ensure the persistent operation below the NOx emission limits imposed by the legislation.

For after-treatment systems such as SCR (selective catalytic reduction) catalysts or LNT (lean NOx traps), not only the knowledge of the tailpipe NOx concentration, but also of the NOx concentration upstream of the system is crucial. This concentration can be obtained using a second NOx sensor, or it can be calculated using sensor information of the engine, such as pressures, temperatures, fuel quantity, engine speed, etc. Additionally, the ambient humidity is a crucial quantity, because it significantly influences the NOx emissions. Increasing ambient humidity leads to decreasing NOx emissions. The reason is the reduced relative oxygen concentration with higher ambient humidity, which leads to lower local flame temperatures in the combustion cycle.

In particular, when only one NOx sensor is used downstream of an after-treatment device and additionally the calculation of the NOx concentration upstream is performed, the two can be compared during phases of catalyst deactivation in order to monitor the accuracy of the NOx sensor. However, since the calculation of the NOx emissions directly depends on the reading of the humidity sensor, an independent monitoring of the humidity sensor is required.

As said above, NOx, Lambda or oxygen sensors are widely used in combustion engines in the exhaust gas line or even in the air intake region. Additionally, certain sensors such as NOx sensors also provide a lambda and/or oxygen signal. Therefore the monitoring of the ambient humidity sensor can be made by determination of the ambient humidity deriving from the oxygen measurement of other sensors in the engine, such as those NOx, Lambda or oxygen sensors.

For the purpose of the present invention, the position of the NOx, lambda or oxygen measurement device can be anywhere in the exhaust or intake system of the engine, even downstream of the after-treatment system, if any.

FIG. 1 shows a non limiting example of a typical engine system setup with potential positions of ambient humidity and NOx, lambda or oxygen sensors. A typical engine system includes an intake pipe 1, which is connected to the output pipes of an intercooler 2 and an EGR cooler 3. The exhaust pipe 4 of the engine is brought to the input of the EGR cooler and of the turbine 5, the output of which goes to the after-treatment system. The input of the intercooler 2 comes from the compressor 6 powered by the turbine.

Other configurations of the engine system are possible, for example without EGR system, or with a two-stage turbine, with or without after-treatment system, etc . . .

A humidity sensor 7 can be placed at the input of the compressor 6 or at the intake pipe 1.

One or more oxygen or lambda or NOx sensors 8 can be placed at the output pipes of the EGR cooler 3 (if present) or intercooler 2, or at the output of the turbine 5, or anywhere downstream of the turbine, i.e. upstream and downstream of any device (catalyst, filter, etc.) in the after-treatment system.

If a two-stage turbine is present, the Oxygen or lambda sensor can be placed in between the two turbines, or at the output of the two-stage turbine.

Since the ambient humidity is inversely proportional to the ambient oxygen concentration, the reading of the oxygen measurement of the NOx, lambda or oxygen sensor reflects the ambient humidity. However, this effect is only visible within a small range of values and with an accurate calibration of the oxygen sensor, which render the operation difficult.

For example, the ambient humidity in Europe varies between approximately 1 and 20 g/kg. This corresponds to a concentration of water in the ambient air of approximately 0.16% to 3.2%. Since the oxygen/nitrogen ratio of air is approximately 20/80, this results in an oxygen concentration variation of approximately 0.032% to 0.67%.

Therefore, a well-defined condition is necessary, where variations in the oxygen measurement can be determined, which corresponds to the ambient humidity, namely a known, well-defined condition, where the drift or offset of the lambda/NOx/oxygen sensor can be related to the variation of the ambient humidity.

A possible non-limiting example is to use the condition of fuel cut-off. During this phase, mostly air is present in the exhaust line. Under these conditions, the oxygen measurement of the NOx, lambda or oxygen sensor signal is slowly adjusted such that it corresponds to a well-defined oxygen concentration, e.g. 20.9%, which is the oxygen concentration of air, if dry air is assumed as the reference.

The offset, which results from this adaptation, is dominantly dependent on the ambient humidity. Therefore, the validity of the humidity signal can be monitored using the offset of an adaptation algorithm.

Figure 2:
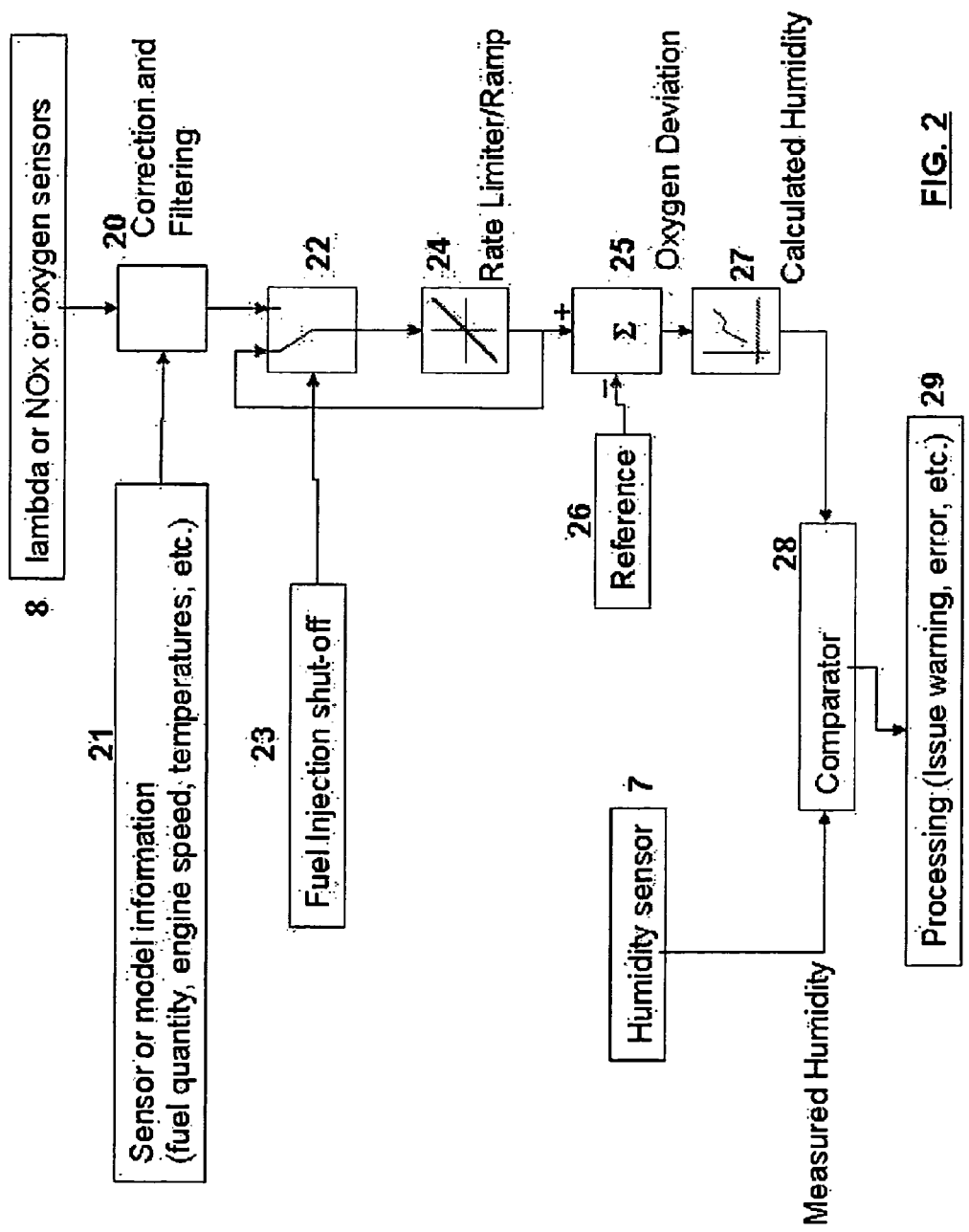
FIG. 2 shows a flow-chart of the monitoring operations as an adaptation algorithm.

With reference to FIG. 2 a non limiting example of a block diagram of a possible adaptation algorithm is given.

The oxygen measured value at the output of a lambda or NOx or oxygen sensor 8 is eventually corrected and filtered in a block 20 according to sensor or model information 21 depending on specific conditions in the engine, such as fuel quantity, air quantity, gas pressure, engine speed, temperature, etc.

The eventually corrected or filtered value is taken in the condition of fuel injection cut-off (or any other well-defined operating condition, where the influence of the ambient humidity can be extracted) through a controller 22 of the cut-off condition 23, and is brought to a control block 24 for limiting the range of values to the output, which loops backwards to the other input of the cut-off controller, for conditions out of the cut-off. The output of the control block is checked (25) for difference with respect to a reference oxygen value set-up 26 for output of the sensor in the cut-off condition: the difference is converted (27) into a value of calculated humidity which is compared (28) with the humidity value measured by the humidity sensor 7. The difference, with or without threshold, gives the offset which can be used for issuing a warning or error signal 29.

The above described method for the determination of the ambient humidity is completely independent from the humidity sensor and therefore acceptable for monitoring purposes.

The processing of the validity of the humidity signal can be advantageously implemented in an ECU (Electronic Control Unit) of the engine.

Therefore this invention can be implemented advantageously in a computer program comprising program code means for performing one or more steps of such method, when such program is run on a computer. For this reason the patent shall also cover such computer program and the computer-readable medium that comprises a recorded message, such computer-readable medium comprising the program code means for performing one or more steps of such method, when such program is run on a computer.

Many changes, modifications, variations and other uses and applications of the subject invention will become apparent to those skilled in the art after considering the specification and the accompanying drawings which disclose preferred embodiments thereof. All such changes, modifications, variations and other uses and applications which do not depart from the spirit and scope of the invention are deemed to be covered by this invention.

Further implementation details will not be described, as the man skilled in the art is able to carry out the invention starting from the teaching of the above description.

What is claimed is:

1. A method for monitoring the humidity sensor in a combustion engine system, comprising the steps of:
  receiving a measured ambient humidity measured by said humidity sensor;
  determining a calculated ambient humidity from an oxygen measurement of at least another sensor in the engine system; and
  comparing the measured ambient humidity with the calculated ambient humidity, and issuing a warning or error signal if the difference between the measured ambient humidity and the calculated ambient humidity exceeds a predetermined threshold;
  wherein the step of determining a calculated ambient humidity is performed by receiving an oxygen measured value signal from the at least another sensor, correcting and filtering the oxygen measured value signal according to one or more of a detected fuel quantity, air quantity, gas pressure, engine speed, or temperature condition, inputting a portion of the corrected and filtered oxygen measured value signal corresponding to the combustion engine system being in a fuel injection cut-off condition into a rate limiter function to output an oxygen measured value, and comparing the oxygen measured value to a reference oxygen value, the calculated ambient humidity being determined according to the difference between the oxygen measured value and the reference oxygen value.

2. The method as in claim 1, wherein said at least another sensor comprises a NOX, or Lambda and/or an oxygen sensor.

3. A system for monitoring a humidity sensor in a combustion engine having an exhaust system, the system comprising a humidity sensor, and at least another sensor for measuring oxygen in the exhaust system, the system being configured to perform the steps of:
   receiving a measured ambient humidity measured by the humidity sensor:
   determining a calculated ambient humidity from an oxygen measurement of the least another sensor; and
   comparing the measured ambient humidity with the calculated ambient humidity, and issuing a warning or error signal if the difference between the measured ambient humidity and the calculated ambient humidity exceeds a predetermined threshold;
   wherein the step of determining a calculated ambient humidity is performed by receiving an oxygen measured value signal from the at least another sensor, correcting and filtering the oxygen measured value signal according to one or more of a detected fuel quantity, air quantity, gas pressure, engine speed, or temperature condition, inputting a portion of the corrected and filtered oxygen measured value signal corresponding to the combustion engine system being in a fuel injection cut-off condition into a rate limiter function to output an oxygen measured value, and comparing the oxygen measured value to a reference oxygen value, the calculated ambient humidity being determined according to the difference between the oxygen measured value and the reference oxygen value.

4. The device as in claim 3, wherein said at least another sensor comprises a NOX, or Lambda and/or an oxygen sensor.

* * * * *